(12) United States Patent
Talutis

(10) Patent No.: US 6,995,563 B2
(45) Date of Patent: Feb. 7, 2006

(54) NONMETALLIC PROCESS CONNECTION

(75) Inventor: Stephen B. Talutis, Milton, MA (US)

(73) Assignee: Invensys Systems, Inc., Foxboro, MA (US)

( * ) Notice: Subject to any disclaimer, the term of this patent is extended or adjusted under 35 U.S.C. 154(b) by 0 days.

(21) Appl. No.: 11/053,449

(22) Filed: Feb. 8, 2005

(65) Prior Publication Data

US 2005/0179439 A1 Aug. 18, 2005

Related U.S. Application Data

(60) Provisional application No. 60/545,156, filed on Feb. 17, 2004.

(51) Int. Cl.
G01N 27/02 (2006.01)

(52) U.S. Cl. ............. 324/439; 324/449; 324/445

(58) Field of Classification Search ........... 324/439, 324/444, 445, 449
See application file for complete search history.

(56) References Cited

U.S. PATENT DOCUMENTS

| | | | |
|---|---|---|---|
| 3,404,335 A * | 10/1968 | Kidder | ............. 324/445 |
| 3,914,002 A | 10/1975 | Berliner et al. | |
| 4,565,619 A | 1/1986 | Gardner et al. | |
| 4,820,990 A | 4/1989 | Moore | |
| 5,006,286 A | 4/1991 | Dery et al. | |
| 5,082,338 A | 1/1992 | Hodge | |
| 5,157,332 A | 10/1992 | Reese | |
| 5,585,729 A | 12/1996 | Toshima et al. | |
| 5,913,451 A | 6/1999 | Madison | |
| 6,340,032 B1 | 1/2002 | Zosimadis | |
| 6,402,205 B1 | 6/2002 | Rose et al. | |
| 6,409,225 B1 | 6/2002 | Ito | |
| 6,442,012 B2 | 8/2002 | Koike et al. | |
| 6,653,841 B1 | 11/2003 | Koerdt et al. | |
| 2004/0012395 A1 * | 1/2004 | Salamitou | ............. 324/444 |

FOREIGN PATENT DOCUMENTS

GB 0 408 247 7/1990

OTHER PUBLICATIONS

Invensys—Foxboro Company Brochure, 871FT Flow-Through Sensor (6 Sheets).
Patent Abstracts of Japan 01074382 (Japanese Patent Document No.64-74382).

* cited by examiner

Primary Examiner—Vincent Q. Nguyen
(74) Attorney, Agent, or Firm—Sampson & Associates, P.C.

(57) ABSTRACT

A sensor includes primary and secondary toroids disposed in spaced, coaxial relation to one another with a process flow path extending therethrough. Electrically conductive and non-metallic connectors are located at opposite ends of the flow path to physically contact the process fluid flowing therethrough. The primary toroid is configured to induce an electric current in the process fluid as the process fluid passes through the flow path, wherein the current varies with conductivity of the process fluid. The secondary toroid is configured to detect the electric current in the process fluid as the process fluid passes through the flow path, the current being proportional to the conductivity of the process fluid.

18 Claims, 4 Drawing Sheets

NONMETALLIC PROCESS CONNECTION

This application claims benefit of provisional application 60/545,156, filed Feb. 17, 2004.

BACKGROUND

1. Technical Field

This invention relates to process control systems, and more particularly to noninvasive toroidal-type conductivity sensors.

2. Background Information

Throughout this application, various publications, patents and published patent applications may be referred to by an identifying citation. The disclosures of the publications, patents and published patent applications referenced in this application are hereby incorporated by reference into the present disclosure.

Flow-through electrodeless conductivity sensors are commonly used to measure various parameters of fluids flowing through a manufacturing process. For example, the 871FT™ Conductivity Sensors (Invensys, PLC) are commercially available non-invasive assemblies suitable for a broad range of conductivity and concentration measurement applications. These 871FT sensors are currently available in several line sizes from ½ inch up to 4 inch. They offer a wide choice of wetted parts materials and end connections, including both industrial and sanitary types.

Unlike conventional insertion type sensors, these flow-through sensors are integrated with the process piping, to provide for conductivity measurement in a non-invasive manner. Self-cleaning is provided due to the tubular design geometry. Calibration of the 871FT sensors may be accomplished in-line through use of a built-in calibration port. In-line calibration is beneficial in applications that use aggressive chemicals and others (e.g., pharmaceuticals) in which opening the process line is undesirable due to concerns of potential contamination.

The 871FT sensors may use an optional temperature detector (e.g., Resistive Temperature Detector (RTD)) for automatic temperature compensation. These sensors are compatible with conventional data transmitters and analyzers for use in factory automation networks.

The 871FT sensors rely on metallic end connections to provide electrical continuity with the process solution in order to generate the desired conductivity data. These metallic portions, however, generally render the sensors unsuitable for use in many applications, such as those that use highly corrosive process solutions. For example, corrosive agents commonly used in semiconductor fabrication processes as etchants, such as HF (Hydrofluoric) Acid, are highly reactive with, and thus tend to corrode, metallic components.

These conventional sensors tend also to be incompatible with many high purity processes which may be particularly sensitive to contamination from metals.

Thus, a need exists for an improved flow-through electrodeless sensor suitable for use in highly corrosive environments and/or in environments that demand a relatively high degree of purity.

SUMMARY

One aspect of the invention includes a sensor having a toroid assembly of primary and secondary toroids disposed in spaced, coaxial relation to one another with a process flow path extending through the assembly. Electrically conductive and non-metallic connectors are located at opposite ends of the flow path. The primary toroid is configured to induce an electric current in the process fluid as the process fluid passes through the flow path, wherein the current varies with conductivity of the process fluid. The secondary toroid is configured to detect the electric current in the process fluid as the process fluid passes through the flow path, the current being proportional to the conductivity of the process fluid.

Another aspect of the invention is similar to the foregoing aspect, while also including a signal port for connecting the toroid assembly to a process variable transmitter. In addition, an electrically non-conductive housing defines the flow path and the connectors are configured for disposition in physical contact with the process fluid flowing therethrough.

A further aspect of the invention includes a method for fabricating a toroidal fluid conductivity sensor, the method includes placing primary and secondary toroids in spaced, coaxial relation to one another, extending a process flow path through the toroids, and placing first and second non-metallic electrically conductive connectors at opposite ends of the flow path. The method also includes configuring the primary toroid to induce an electric current in the process fluid, and configuring the secondary toroid to detect the current in the process fluid as the process fluid passes through the flow path, the induced current being proportional to the conductivity of the process fluid.

A still further aspect of the invention includes a method for measuring the conductivity of a fluid. The method includes providing the sensor of the first aspect of the invention described above, coupling the connectors in series with a fluid flow conduit, and electrically coupling the electrically conductive non-metallic connectors to one another. The method further includes inducing, with the primary toroid, an electric current in process fluid passing through the sensor, and detecting, with the secondary toroid, the current in the process fluid as the process fluid passes through the sensor, the current being proportional to the conductivity of the process fluid.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

Figure 1:
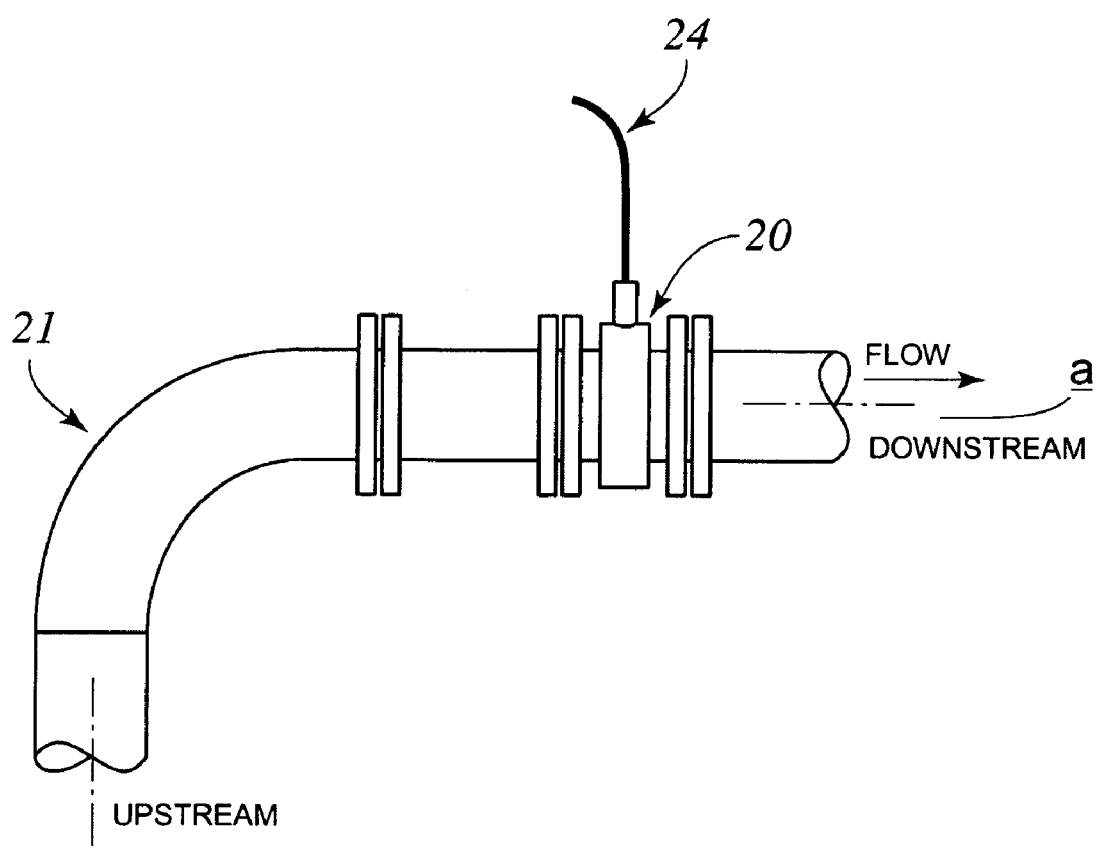
FIG. 1 is an elevational schematic view, with portions broken away, of an embodiment of the present invention in a representative installation.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings shall be indicated with like reference numerals and similar features as shown in alternate embodiments in the drawings shall be indicated with similar reference numerals.

Turning now to FIG. 1, an exemplary embodiment of the present invention, sensor 20, is shown in a typical installation, within a fluid process conduit 21. Process solution flows through the conduit 21 and through sensor 20, in a downstream direction indicated by arrow a.

Figure 2:
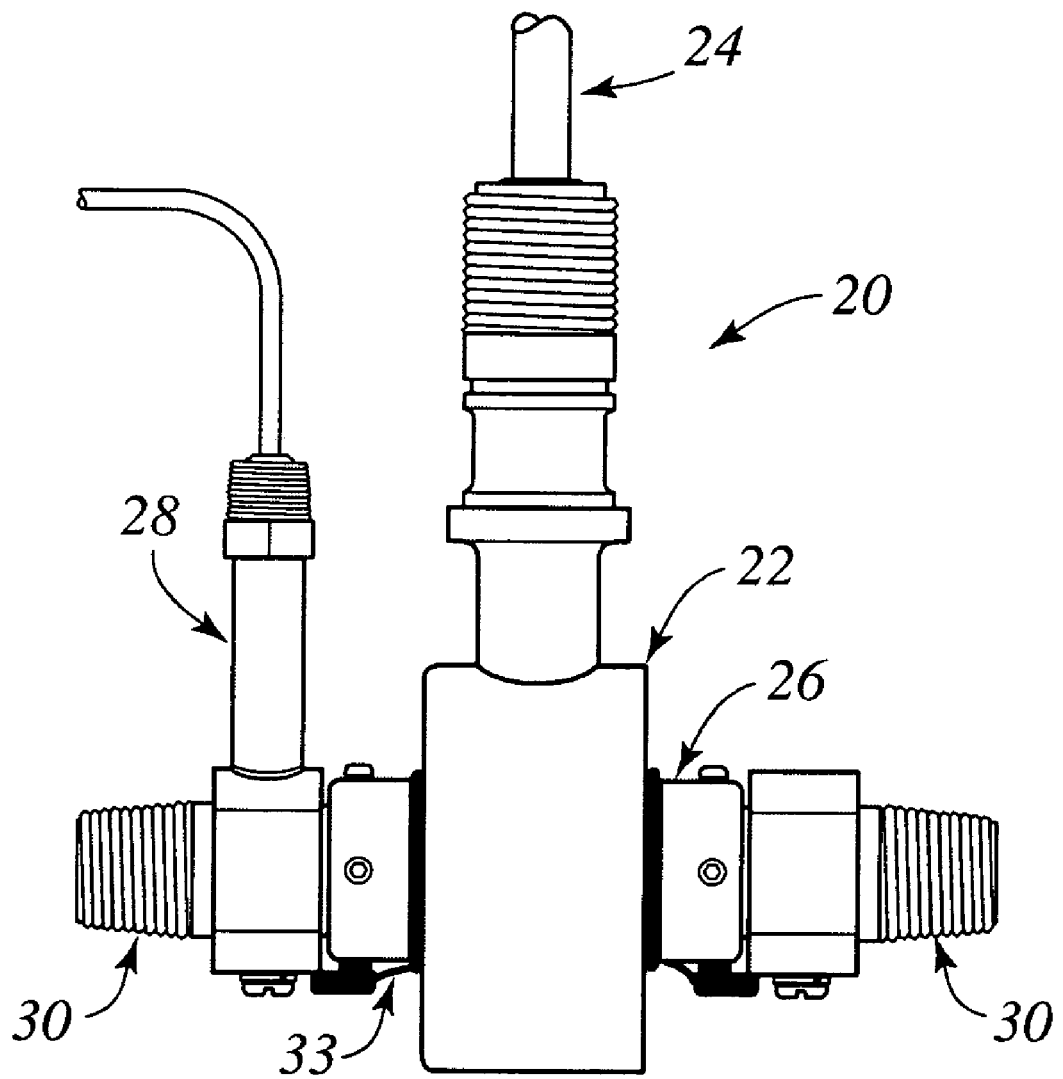
FIG. 2 is an elevational schematic view, on an enlarged scale, of an embodiment of the present invention.

Turning to FIG. 2, sensor 20 includes many components common to a conventional 871FT Conductivity Sensor, including a toroid assembly 22, an output cable 24 for connection to a conventional process variable transmitter and/or analyzer 46 (FIG. 4), a non-metallic insulator 26, and optionally, an integral probe 28, such as a temperature detector.

Figure 4:
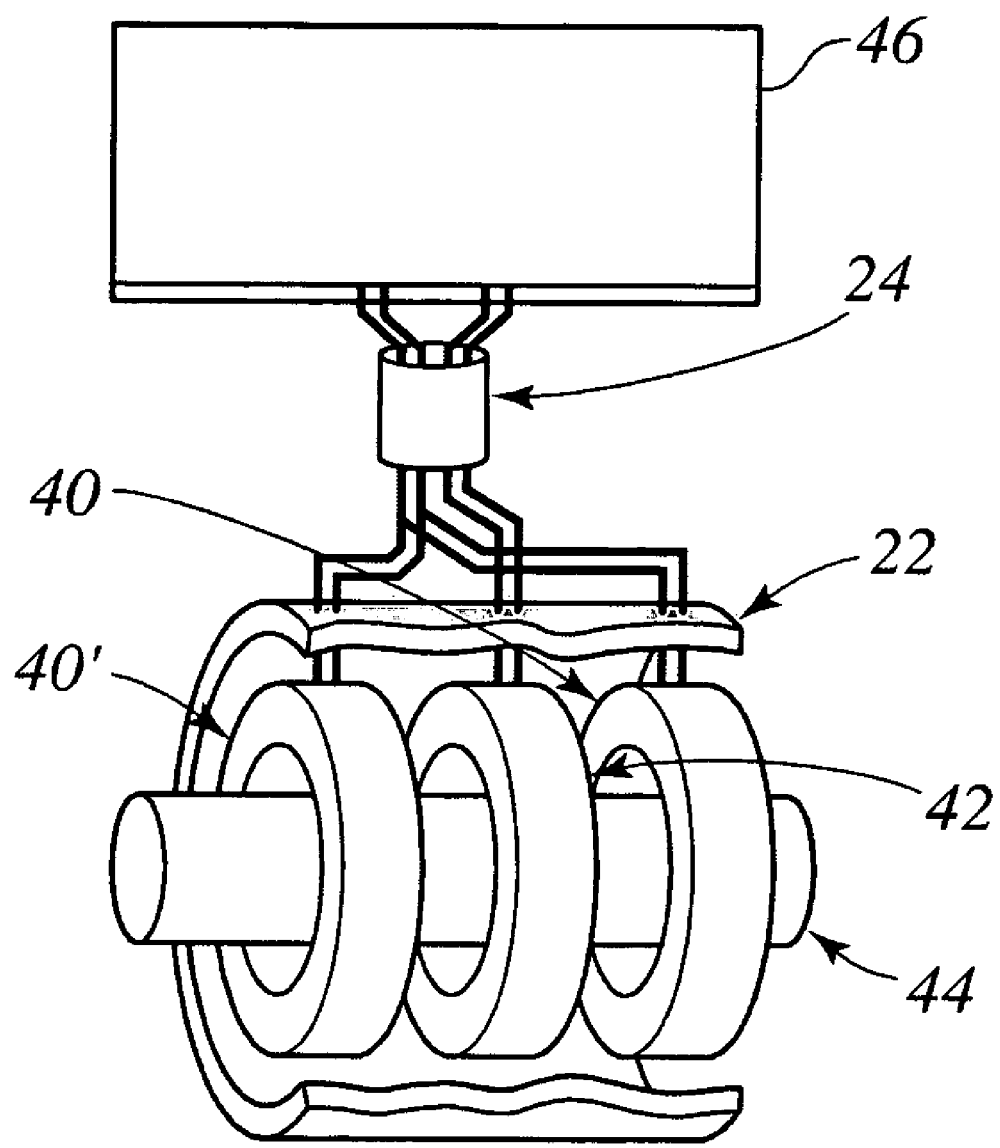
FIG. 4 is an elevational schematic view, with portions broken away, and portions shown in phantom, of portions of an embodiment of the present invention.

Referring to FIG. 4, sensor 20 operates in a conventional manner, such as described in U.S. Pat. No. 5,157,332. As shown, primary and secondary inductive toroids 40 and 42, respectively, are mounted in the toroid assembly 22 coaxially with a flow path defined by a housing 44. Additional toroids, such as additional primary toroid 40' shown in phantom, may be optionally provided, such as to enhance various operational characteristics.

The primary toroid(s) induce an electric current in the process fluid as it passes therethrough. The voltage created, which varies with process fluid conductivity, is detected by the secondary toroid and converted to a conductivity measurement. Advantageously, the smooth bore through toroid assembly 22 enables sensor 20 to provide a noninvasive measurement of conductivity. An optional temperature sensor 28 (FIG. 2) may be used to compensate the conductivity measurement for the temperature of the process fluid.

Figure 3:
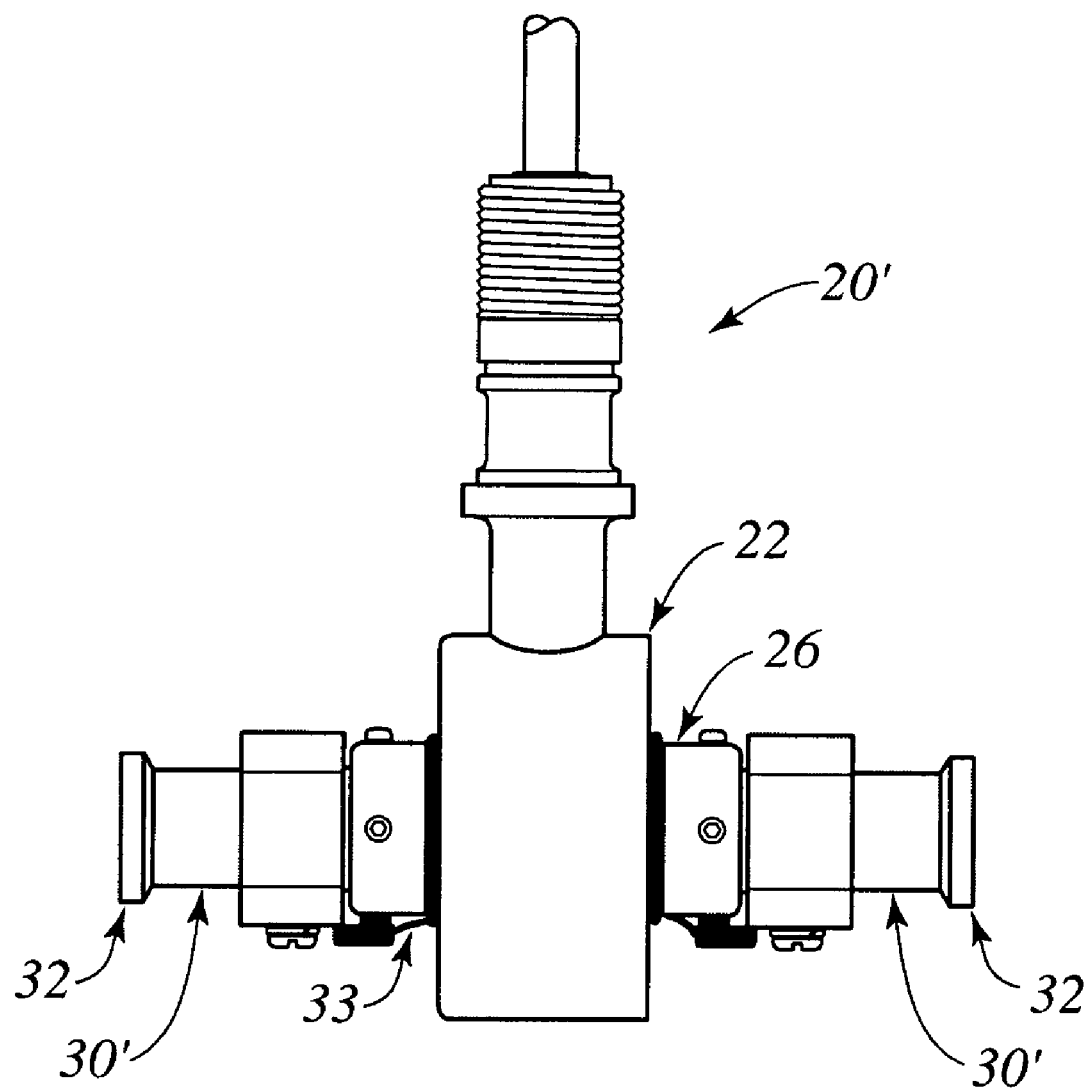
FIG. 3 is a view similar to that of FIG. 2, of an alternate embodiment of the present invention.

Turning now to FIGS. 2 and 3, end connectors 30, 30' disposed at opposite ends of housing 44, couple the housing in series within flow conduit 21 (FIG. 1). These end connectors (also referred to as process fittings) 30, 30' are also electrically conductive, and in the embodiments shown, are non-metallic. Their electrical conductivity enables connectors 30, 30' to provide electrical continuity with the process solution to facilitate generation of the desired conductivity data. The connectors at both ends are electrically coupled to one another, such as with a cable 33, to provide a complete electrical circuit, to facilitate accurate conductivity measurement. In addition, the non-metallic nature of connectors 30, 30' enables them to be used with process solutions that are generally incompatible with metals or applications which may be sensitive to metallic contamination.

For example, sensors 20, 20' thus may be used in semiconductor fabrication processes that use HF acid or other caustic fluids as etchants, etc. Sensors 20, 20' may also be used in high purity, sanitary applications which may be sensitive to metal contamination.

Exemplary connectors 30, 30' may be fabricated from electrically conductive (carbon-impregnated, for example) polymers such as PTFE (e.g., TEFLON®, DuPont), Fluorine-containing synthetic resins (e.g., KYNAR®, Atofina Chemicals, Inc.), PEEK, and other conductive plastics. In the particular embodiment shown, connectors 30 are provided with exterior threads to facilitate coupling to conventional piping systems 21. Moreover, although carbon is impregnated into these non-metallic materials to provide the desired conductivity, those skilled in the art should recognize that substantially any non-metallic conductive material that may be currently available or developed in the future, may be used without departing from the spirit and scope of the present invention.

Turning specifically to FIG. 3, an alternate embodiment of the invention, shown as sensor 20', is substantially similar to sensor 20, though instead of external threads, uses connectors 30' having terminal flanges 32 for coupling to mating flanges of piping system 21.

These flanged connectors 30' are useful, for example, in conventional sanitary applications. Although shown without it in this Figure, sensor 20' may be used with or without optional temperature detector 28 (FIG. 2).

Although embodiments of the subject invention have been shown and described having threaded and flanged connections, those skilled in the art should recognize that connectors configured in substantially any manner capable of coupling to a process fluid connection may be used, including for example, but not limited to, those commonly known as Tri-clamp, sanitary, flange, pipe (e.g., threaded) fitting, hose and tube connections, etc., without departing from spirit and scope of the present invention.

Moreover, although embodiments of the instant invention have been shown and described in the context of a modified 871FT toroidal sensor, the skilled artisan should recognize that nominally any type of toroidal conductivity sensor may be used in combination with conductive non-metallic connectors as described herein, without departing from the spirit and scope of the present invention.

In the preceding specification, the invention has been described with reference to specific exemplary embodiments thereof. It will be evident that various modifications and changes may be made thereunto without departing from the broader spirit and scope of the invention as set forth in the claims that follow. The specification and drawings are accordingly to be regarded in an illustrative rather than restrictive sense.

Having thus described the invention, what is claimed is:

1. An electrodeless conductivity sensor comprising:
    a toroid assembly including at least primary and secondary toroidal electromagnetic coil windings disposed in spaced, coaxial relation to one another;
    a signal port coupled to said toroid assembly, said signal port configured for connection to a process variable transmitter;
    a housing defining a process flow path extending coaxially through, while being spaced from, said toroid assembly;
    said housing being electrically non-conductive;
    first and second connectors disposed at first and second ends of said flow path, respectively;
    said connectors being electrically conductive and non-metallic;
    said connectors configured for series coupling within a fluid flow conduit, wherein said connectors and said process flow path are configured to enable a process fluid to flow therethrough;
    wherein said connectors are configured for disposition in physical contact with the process fluid flowing therethrough;
    said primary toroid configured to induce an electric current in the process fluid as the process fluid passes through said flow path, wherein the current varies with conductivity of the process fluid; and
    said secondary toroid configured to detect the electric current in the process fluid as the process fluid passes through said flow path, the current being proportional to the conductivity of the process fluid.

2. A sensor comprising:
a toroid assembly including at least primary and secondary toroids disposed in spaced, coaxial relation to one another;
a process flow path extending through said toroid assembly;
first and second connectors disposed at first and second ends of said flow path, respectively;
said connectors being electrically conductive and non-metallic;
said primary toroid configured to induce an electric current in the process fluid as the process fluid passes through said flow path, wherein the current varies with conductivity of the process fluid; and
said secondary toroid configured to detect the electric current in the process fluid as the process fluid passes through said flow path, the current being proportional to the conductivity of the process fluid.

3. The sensor of claim 2, wherein said toroids comprise electromagnetic coil windings.

4. The sensor of claim 2, comprising a signal port coupled to said toroid assembly, said signal port configured for connection to a process variable transmitter.

5. The sensor of claim 2, comprising a signal port coupled to said toroid assembly, said signal port configured for connection to a signal analyzer.

6. The sensor of claim 2, wherein the process flow path is defined by a housing extending coaxially through said toroid assembly.

7. The sensor of claim 6, wherein said housing is electrically non-conductive.

8. The sensor of claim 2, wherein said connectors are configured for disposition in physical contact with process fluid flowing through said flow path.

9. The sensor of claim 8, wherein said connectors are electrically isolated from said toroid assembly.

10. The sensor of claim 9, wherein said connectors are electrically connected to one another.

11. The sensor of claim 2, wherein said connectors are configured for series coupling within a fluid flow conduit, so that said connectors and said process flow path are configured to enable a process fluid to flow therethrough.

12. The sensor of claim 2, wherein said connectors are fabricated from an electrically conductive non-metallic polymer.

13. The sensor of claim 12, wherein said electrically conductive non-metallic polymer comprises an impregnated polymer, impregnated with an electrically conductive medium.

14. The sensor of claim 13, wherein said electrically conductive medium comprises carbon.

15. The sensor of claim 13, wherein said impregnated polymer comprises a material selected from the group consisting of impregnated: PTFE; synthetic fluorine-containing resins; PEEK; and combinations thereof.

16. A method for measuring the conductivity of a fluid, the method comprising:
(a) providing a sensor as recited in claim 2;
(b) coupling the connectors in series with a fluid flow conduit;
(c) electrically coupling the conductive non-metallic connectors to one another;
(d) inducing, with the primary toroid, an electric current in process fluid passing through the sensor, wherein the current varies with conductivity of the process fluid; and
(e) detecting, with the secondary toroid, the current in the process fluid as the process fluid passes through the sensor, the current being proportional to the conductivity of the process fluid.

17. A sensor comprising:
primary toroid means for inducing an electric current in a process fluid passing within a flow path, wherein the current varies with conductivity of the process fluid;
secondary toroid means for detecting the electric current in the process fluid passing within the flow path, the current being proportional to the conductivity of the process fluid;
first and second connection means disposed at first and second ends of the flow path, respectively; and
said connection means being electrically conductive and non-metallic.

18. A method for fabricating a toroidal fluid conductivity sensor, the method comprising:
(a) disposing primary and secondary toroids in spaced, coaxial relation to one another;
(b) extending a process flow path through the toroids;
(c) disposing first and second electrically conductive, non-metallic connectors at opposite ends of the flow path;
(d) configuring the primary toroid to induce an electric current in the process fluid as the process fluid passes through the flow path, wherein the current varies with conductivity of the process fluid; and
(e) configuring the secondary toroid to detect the current in the process fluid as the process fluid passes through said flow path, the current being proportional to the conductivity of the process fluid.

* * * * *